United States Patent [19]

Itoh et al.

[11] Patent Number: 5,080,917

[45] Date of Patent: Jan. 14, 1992

[54] ORAL COMPOSITIONS FOR RUMINANTS

[75] Inventors: Kunio Itoh; Kiyoshi Sugiyama; Motohiro Ohta, all of Shizuoka, Japan

[73] Assignee: Kyowa Hakko Kogyo Kabushiki Kaisha, Tokyo, Japan

[21] Appl. No.: 333,170

[22] Filed: Apr. 3, 1989

[30] Foreign Application Priority Data

Apr. 5, 1988 [JP] Japan .................................. 63-83887

[51] Int. Cl.$^5$ .............................................. A23K 1/00
[52] U.S. Cl. ........................................ 426/96; 426/72; 426/74; 426/302; 426/303; 426/520; 426/601; 426/656; 426/807
[58] Field of Search ................. 426/96, 807, 302, 601, 426/72, 656, 74, 303, 520, 519; 424/489, 482

[56] References Cited

U.S. PATENT DOCUMENTS

| | | | |
|---|---|---|---|
| 4,196,187 | 4/1980 | Dannelly et la. | 424/489 |
| 4,533,557 | 8/1985 | Maruyama et al. | 426/72 |

FOREIGN PATENT DOCUMENTS

| | | |
|---|---|---|
| 48-1278 | 4/1973 | Japan . |
| 54-46824 | 4/1979 | Japan . |
| 54-46825 | 4/1979 | Japan . |
| 59-66843 | 4/1984 | Japan . |
| 61-88843 | 5/1986 | Japan . |
| 61-88844 | 5/1986 | Japan . |

OTHER PUBLICATIONS

Hawley "The Condensed Chemical Dictionary" 10th. Edition Van Nostrand Reinhold Publishers New York, N.Y., 1982 pp. 840, 1084.

Primary Examiner—R. B. Penland
Attorney, Agent, or Firm—Schweitzer Cornman & Gross

[57] ABSTRACT

A coating agent for delaying the release of a physiologically active substance to be administered per os to ruminants, said coating comprising a veterinary acceptable water-soluble, synthetic high molecular compound and ethylcellulose, said coating agent being stable in the first stomach or rumen of ruminants and capable of being effectively disintegrated for subsequent absorption in the 4th stomach of ruminants, characterized in that said coating agent further comprises at least one substance which is miscible with both of said high molecular weight compound and ethylcellulose and is insoluble in water.

Said coating agent forms a coat which protects the active substance from degradation in the first stomach of a ruminant at a pH of about 5.5 and rapidly breaks down in the 4th stomach at a pH of about 3, thereby releasing the active ingredient for absorption by the animal.

The coating agent and the actives coated therewith and their preparation are described.

14 Claims, No Drawings

ORAL COMPOSITIONS FOR RUMINANTS

The present invention relates to oral compositions for ruminants and more specifically relates to delayed-release coating agents for the preparation of supplements to feedstuffs for ruminants which comprises a core of at least one physiologically active substance. The present invention also relates to supplements to ruminant feedstuffs formulated with such coating agents.

It is known that the pH in the first stomach the rumen of a ruminant is about 5.5 and that various microorganisms exhibit fermentation activity in the first stomach where feedstuffs are retained for about 6 to 30 hours. It is also known that in cases where veterinary acceptable, physiologically active substances (hereinafter referred to as active substances) such as, amino acids are given per os to ruminants such as, cattle and sheep, effective absorption of the active substances in the 4th stomach, having a pH of about 3, and the following digestive tract is much reduced because they have been degraded while in the first stomach.

In order to obviate this problem, various proposals have hitherto been made to protect the active substances. For example, the provision of a core of active substance covered with a coating agent which is capable of inhibiting the decomposition of the active substances in the first stomach and the following digestive tract, and which does not inhibit absorption in the 4th stomach and the following digestive tract, have been suggested.

Examples of such proposals include the use of an additive to feedstuffs, which is formulated into a capsule prepared by using a coating agent which comprises triglycerides, such as hydrogenated fats originating from plants and animals, waxes and mixture thereof [as disclosed in Japanese Patent Application-A-12785/73]. An additive to feedstuffs formulated into a pellet containing a mixture of an active substance and a basic substance (for example, magnesium oxide, magnesium carbonate, calcium carbonate and aluminium hydroxide) and coated with a coating agent comprising a polymer (for example, a copolymer of cellulose propionate morpholinobutylate or dialkylaminoethyl acrylate with methacrylate) is disclosed in Japanese Patent Application-A-46824/79. An additive to feedstuff containing an active substance and coated with a coating agent comprising a high molecular compound (for example, cellulose propionatemorpholinolactate, a copolymer of vinylpyridine with styrene and a copolymer of 2-methyl-5-vinylpyridine with styrene or acrylonitrile) and a hydrophobic substance (for example, oleic acid, stearic acid and palmitic acid) is disclosed in Japanese Patent Application-A-46825/79. An additive to feedstuff coated with a coating agent comprising chitosan and at least one member selected from saturated or unsaturated monocarboxylic acids having 14-22 atoms and hardened animal fats is disclosed in U.S. Pat. No. 4,533,557. An additive to feedstuffs coated with a coating agent comprising chitosan, an inorganic salt and at least one member selected from saturated or unsaturated monocarboxylic acids having 14-22 atoms and hardened animal fats is disclosed in Japanese Patent Application-A-66843/84. An additive to feedstuffs coated with a coating agent comprising ethylcellulose and a synthetic high molecular compound which is soluble in water at a pH of not higher than 5 is disclosed in Japanese Patent Application-A-88843/86. An additive to feedstuffs has been prepared by using a coating agent which comprises a first component, viz. a synthetic high molecular compound which is soluble in water at a pH of not higher than 5 and a second component viz. at least one member selected from fats, waxes, saturated or unsaturated aliphatic alcohols having 14-32 carbon atoms and saturated or unsaturated fatty acids having 14-37 carbon atoms [as disclosed in Japanese Patent Application-A-88844/86].

The provision of an improved coating agent is however still required because known coating agents have, in general, either the disadvantages that if it is capable of exerting higher protection in the first stomach then it is only discomposed slowly in the 4th stomach, or it is decomposed rapidly in the 4th stomach but is liable to exert insufficient protection in the first stomach.

THE INVENTION

The present invention is based upon the discovery that the protecting activity of the coating agent disclosed in Japanese Patent Application-A-88843/86 may be improved unexpectedly by using a certain substance which is solid at room temperature, soluble in organic solvents and is insoluble in water.

According to one aspect of the present invention, there is provided a coating agent for delaying the release of a physiologically active substance to be administered per os to ruminants, comprising a veterinary acceptable, water-soluble, synthetic high molecular compound and ethylcellulose, said coating agent being stable in the first stomach of ruminants and capable of being effectively disintegrated in the 4th stomach of ruminants, characterized in that said coating agent further comprises at least one substance which is miscible with both the high molecular weight compound and the ethylcellulose and is insoluble in water.

According to another aspect of the present invention, there is provided a delayed-release veterinary composition for oral administration to ruminants, comprising one or more physiologic active substances coated with an effective amount of a coating agent of the first aspect of the invention.

For the purpose of the present invention, various veterinary acceptable, physiologically active substances of known types may be used. Examples include amino acids such as methionine, lysine, tryptophan, threonine, glutamic acid, glutamine and asparagine; amino acid derivatives or peptides thereof such as dopa glutathione; vitamins such as vitamin A; enzymes such as acidic protease; sugars such as glucose; antibiotics such as penicillin; and anthelmintics such as levamisole. These active substances may be used either alone or in combination and mixture.

The coating agent according to the present invention may be used with advantage for the preparation of feedstuff supplements for various ruminants such as, for example, cattle, sheep and goats.

Veterinary acceptable, high molecular weight compounds which may be used in the coating agent according to the present invention include various known compounds which are wet-proof and soluble in water at a pH of not more than 5. Preferred high molecular compounds are exemplified as follows:

(1) Polyvinyl acetal diethylamino-acetates. Advantageously those having a molecular weight of from 30,000 to 150,000 and containing 1.0-5.5% (w/w) of nitrogen such as, for example, AEA (commercially available from Sankyo K. K. Japan) may be used.

(2) Copolymers formed with dimethylaminoethyl methacrylate and at least one member selected from the alkyl esters of methacrylic acid and alkyl esters of acrylic acid. Advantageously those having a molecular weight of from 50,000 to 500,000 and containing 3-8% (w/w) of nitrogen such as, for example, Eudragit E100 (solid), E12.5 (12.5% suspensions) (copolymers of dimethylaminoethyl methacrylate, methylmethacrylate and butylmethacrylate; commercially available from Rohm Pharma, West Germany) may be used.

(3) Copolymers formed with 2-methyl-5-vinylpyridine and at least one member selected from alyl esters of methacrylic acid and alkyl esters of acrylic acid, methacrylic acid and acrylic acid. Advantageously those having a molecular weight of from 5,000 to 400,000 and containing 2-15% (w/w) of nitrogen such as, for example, MPM-47 (commercial product of Tanabe Seiyaku K. K., Japan; copolymer formed with 2-methyl-5-vinylpyridine, methacrylate and acrylic acid) may be used.

With regard to the above-mentioned monomers, preferred alkyl groups of alkyl esters are exemplified by straight or branched alkyl groups having 1-8 carbon atoms such as ethyl, i-propyl and n-butyl and 2-ethylhexyl groups.

It is preferred to use an ethylcellulose containing 2.0-2.8% (w/w) of an ethoxy group per one unit of glucose.

In order to achieve disintegration of the coating agent in the 4th stomach with good results, various water-insoluble substances which are miscible with both of the above-mentioned high molecular weight compound and ethylcellulose may be used.

It is advantageous to use a water-insoluble substance which is solid at room temperature to aid the manufacture.

Moreover, with regard to formation of a stronger coating layer, it is advantageous to use those which are soluble in various solvents such as, for example, isopropanol, ethanol, dichloromethane, acetone, ethyl acetate and ethylene glycol monoethyl ether. Substances which may be used include, for example, saturated fatty acids having more than 14 carbon atoms, higher aliphatic alcohols having more than 12 carbon atoms, hardened oils of plant or animal origin, natural resins and synthetic resins.

Preferred examples of saturated fatty acids having more than 14 carbon atoms include myristic acid, stearic acid and palmitic acid.

Preferred examples of higher aliphatic alcohols having more than 12 carbon atoms include lauryl alcohol, myristyl alcohol, cetyl alcohol and stearyl alcohol.

Preferred examples of animal and plant oils include hardened (hydrogenated) oil originating from beef tallow and hardened castor oil.

Preferred examples of natural resins and synthetic resins include shellac and polyvinylacetate.

The weight ratio of the high molecular compound to ethylcellulose contained in the coating agent of the present invention may be, for example, from 1:0.5 to 1:10 (particularly from 1:1 to 1:7).

We have found that, in the case where the ratio of ethylcellulose is smaller than 1:0.5, a large amount of the active substances such as, for example, amino acids may be dissolved in the first stomach and the following digestive tract and are thereby available to microorganisms for decomposition while in the other case where the ratio is greater than 1:10, the active substances may not be sufficiently disintegrated and released in the 4th stomach.

The weight ratio of the water-insoluble substance to ethylcellulose may be, for example, from 1:0.1 to 1:20 (preferably from 1:0.5 to 1:2).

Advantageously, the coating agent may be in solid form and may, if desired, contain various known plasticizers such as, for example, polyethylene glycol, triacetin and Wyvacet (commercial product of Eastman Kodak Corpn., U.S.S.); anti-coagulating agents such as, for example, talc and magnesium stearate. The amount of such additives in total is preferably not more than 30% (w/w).

The ratio of the above-mentioned high molecular compound to the water-insoluble substances present in the coating agent is preferably more than 50% (for example, more than 1:0.7) by weight.

Usually, the core may be solid and may, if desired, contain various known binders such as, for example, hydroxypropyl cellulose, polyvinyl pyrrolidone and polyvinyl alcohol; excipients such as, for example, lactose, mannitol and crystalline cellulose; and disintegrants such as, for example, potato starch, corn starch, carboxymethyl cellulose calcium, carboxymethyl cellulose sodium and crystalline cellulose.

The ratio of the coating agent to the active substances coated therewith exerts a significant influence upon the availability and value of the active substances. Thus, for example, it is advantageous to use the coating agent at a weight ratio of 5-100 parts per 100 parts of the core. We have found that, in the case where the amount of the coating agent is insufficient (for example, not more than 5%), the active substances are excessively decomposed or disintegrated in the first stomach, while in the case where the ratio of the coating agent is too high (for example, more than 100 parts), there is insufficient disintegration of the active substances in the 4th stomach.

The oral composition of the present invention may be obtained by drying a granule containing at least one of the active substances and coating the dried granule with a coating agent of the present invention as described hereinbefore.

The granule may be prepared by adding a suitable binder dissolved in a suitable solvent to at least one active substance and kneading the mixture to obtain the desired granule.

The concentration of solids present in the binder solution is, for example, 3-20% w/w.

Granules may be prepared in conventional manner by using a cylindrical or spherical granulator, for example.

It is also possible to prepare granules by coating at least one active substance which is preferably in the form of crystals or formulated spherically.

In the case where at least two active substances are used, it is advantageous to prepare a granule by applying a binder solution onto a core containing a first active substance viz. at least one active substance having a higher solubility in the solvent such as the water to be used for the preparation of the binder solution, and then applying a second or additional active substance having a lower solubility in the solvent onto the coated core, for example, by spray-drying thereby to obtain the desired granule.

Thus, for example, in order to obtain granules containing lysine and methionine, cores are prepared by treating crystalline lysine or granulated lysine by means of a centrifuge-fluidizing granulating machine (for example, CF-granulator, CF-360, commercial product of Freund Sangyo K. K., Japan), to which powders of methionine and an aqueous binder solution are fed to prepare granules containing lysine. The diameter of the core containing the active substance having the higher solubility is, for example, about 0.5-3.0 mm. The resultant granules are then dried, for example, with hot air (for example, at a temperature of 30°-70° C. for 30-90 minutes) to give a preferred diameter (for example, 1.4-3.2 mm).

The active substances may be used alone or in combination with other substances conventionally used in the art such as, for example, excipients and disintegrators and the like.

The dried granules may then be coated, for example, by spray-coating a coating solution having a suitable concentration of solids, for example, 1-10% w/w.

Examples of the solvents which may be used for the preparation of the coating agent of the present invention include those capable of dissolving the water-soluble high molecular compound of the present invention such as dichloromethane, ethanol, isopropanol, acetone, ethyl acetate, which may be used individually or in combination.

In order to improve absorption of the active substances, it is advatageous to effect dissolution of the active substances with higher speed in the 4th stomach. However, use of a coating agent not containing a water-insoluble substance, leads to the disadvantage that the ethylcellulose layer is not disintegrated, even when the synthetic high molecular substance has already been dissolved owing to the solubility of the high molecular compound at the pH in the 4th stomach. Moreover, the strength of the coating agent is liable to decrease rapidly after the dissolution of the high molecular weight compound if an excessively large amount of the water-insoluble substance is used.

It is preferred that a coating agent according to the present invention be wet-proof at a generally neutral pH and may be disintegrated at a lower pH e.g. below 5. Disintegration of the coating agent which is, for example, in the form of a thin layer on the surface of the granule may begin at a relatively low pH because of the use of a water-insoluble substance which is miscible with both the synthetic high molecular compound and ethylcellulose. As a result, the active substances are protected in the first stomach but are dissolved effectively in the 4th stomach.

It is possible to make the coating agent effectively wet-proof and also to limit the amount of the coating agent used and thus improve the value of the coating agent.

The following non-limiting examples and experiments illustrate the present invention.

EXAMPLE 1

400 g of an aqueous solution of polyvinyl alcohol (20% w/w) was added to DL-methionine (2000 g) as a binder. The mixture was well kneaded and then treated using a cylindrical granulating device equipped with a screen to give granules having a diameter of 2.0 mm. The materials were made spherical by using a Marumerizer (a machine, produced by Fuji-Paudaru K. K., Japan) and were then treated by using a sieve of 10-12 meshes. The granules were air-dried at a temperature of 60° C. for one hour to obtain dried granules having a diameter of 1.4-1.8 mm.

Separately, a mixture of ethylcellulose (150 g), stearic acid and AEA (4:2:3 w/w) and glycerol fatty acid (30 g) were dissolved in a mixture of isopropanol and acetone (3000 g;2:1 v/v). Magnesium stearate (25 g; anti-coagulating agent was added thereto to prepare a coating solution. A fluidizing bed was used to apply the coating solution to the above-mentioned granules (1000 g) by spray-coating. The coating agent (10 parts per 100 parts of granules onto the granules to obtain granules containing 90% w/w of methionine.

EXAMPLE 2

Ethylcellulose, polyvinyl acetate and AEA (150 g; 1:1:1 w/w) and glycerol fatty acid ester (30 g) were dissolved in a mixture of ethanol and acetone (3000 g; 3:1 v/v). Magnesium stearate (25 g; anti-coagulating agent) was added thereto to prepare a coating solution. In a similar manner to that described in Example 1, a coating solution (10 parts by weight) containing solids was applied by spray-coating onto 100 parts by weight of the granules (diameter: 1.7-2.4 mm). There were obtained coated granules having a slightly increased diameter and containing 90% w/w of methionine.

COMPARATIVE TEST 1

A mixture of ethylcellulose and AEA 9150 g; 6:3 w/w) and glycerol fatty acid ester (30 g) were dissolved in a mixture of ethanol and acetone (3000 g; 3:1 v/v). Magnesium stearate (25 g; anti-coagulating agent) was added thereto to prepare a coating solution. In a similar manner to that described in Example 1, the resultant coating solution (10 parts by weight) containing solids was applied onto the granules having a diameter of 1.7-2.4 mm (100 parts by weight) by spray-coating. There were obtained granules containing methionine (90% w/w) and protected with the coating agent.

EXAMPLE 3

As a binder, 700 g of an aqueous ethanol (ethanol: water = 1:1 v/v) containing hydroxpropyl cellulose (6% w/w) was added to lysine hydrochloride (2000 g). The mixture was well kneaded and transferred to a cylindrical granulating device equipped with a screen to give granules having a diameter of 2.0 mm, which were then made spherical by using a Marumerizer (a machine, produced by Fuji-Paudaru K. K., Japan) and treated by using a sieve of 8-10 meshes. The granules were air-dried at a temperature of 50° C. for one hour to obtain dried granules having a diameter of 1.7-2.4 mm.

Separately, a mixture of ethylcellulose, stearic acid and Eudragit E100 (150 g; 3:2:1 w/w) and glycerol fatty acid ester (30 g) were dissolved in a mixture of ethanol and acetone (3000 g; 2:1 v/v). Magnesiun stearate (25 g; anti-coagulating agent) was added thereto to prepare a coating solution. A fluidizing bed was used to apply the coating solution to the above-mentioned granules by spray-coating. The coating solution (10 parts per 100 parts of granules on solid basis) was coated onto the granules to obtain granules containing lysine (90% w/w) and protected with the coating agent.

COMPARATIVE TEST 2

A mixture of ethylcellulose and Eudragit E100 (150 g; 5:1 w/w) was dissolved in a mixture of ethanol and acetone (3000 g; 3:1 v/v). Magnesium stearate (25 g; anti-coagulating agent) was added thereto to prepare a coating solution. In a similar manner to that described in Example 3, the coating solution (10 parts by weight)

containing solids was applied onto the granules having a diameter of 1.7-2.4 mm (100 parts by weight) by spray-coating. There were obtained granules containing lysine (90% w/w) and protected with the coating agent.

EXAMPLE 4

A binder solution (700 g) was prepared by adding hydroxypropyl cellulose (6% w/w) to an aqueous ethanol (ethanol:water=1:1 v/v), which was then added to lysine hydrochloride (2000 g). The mixture was well kneaded and treated by using a cylindrical granulating device equipped with a screen to give granules having a diameter of 2.0 mm. The granules were made spherical by using a Marumerizer (a machine, produced by Fuji-Paudaru K. K., Japan) and were then treated using a sieve of 8-10 meshes. The granules were air-dried at a temperature of 60° C. for one hour to obtain dried granules having a diameter of 1.7-2.4 mm.

Separately, a mixture of ethylcellulose, polyvinyl acetate and AEA (150 g; 5:1:3 w/w) were dissolved in a mixture of dichloromethane and ethanol (300 g; 3:3 v/v) to prepare a coating solution. The solution (10 parts per 100 parts of granules on solid basis) was applied onto the granules by spray-drying to obtain coated granules containing 90% w/w of methionine.

COMPARATIVE TEST 3

A mixture of ethylcellulose and AEA (150 g; 6:3 w/w) was dissolved in a mixture of dichloroethane and ethanol (3000 g; 1:1 v/v) to prepare a coating solution. In a similar manner to that described in Example 4, the coating solution (10 parts per 100 parts of granules by weight on solid basis) was coated onto the granules to obtain granules containing lysine (90% w/w) and protected by the coating agent.

EXAMPLE 5

Crystals of lysine (1500 g) having a diameter of 1.5-2.0 mm were put into CF-granulator (CF-360, commercial product of Freund Sangyo K. K., Japan), to which were then applied powders of methionine (1500 g) and a solution of polyvinyl alcohol (containing 90 g of polyvinyl alcohol and 510 g of water) to prepare methionine coated granules. The resultant granules were air-dried at a temperature of 60° C. for one hour to obtain dried granules having a diameter of 1.5-3.0 mm. A fluidizing bed was used to apply to the granules a coating solution prepared in a similar manner to that described in Example 2 to obtain granules protected with the coating agent (10 parts per 100 parts of granules on solid basis) containing each 44% w/w of lysine and methionine.

COMPARATIVE TEST 4

A binder solution was prepared by dissolving polyvinyl alcohol (90 g) in water (450 g). The binder solution was combined with a mixture of powders of both methionine and lysine (each 1500 g). The mixture was well kneaded for 10 minutes using a ribbon-type kneader. The material was then treated by using a cylindrical granulator equipped with a screen to give granules having a diameter of 2.0 mm, which were made spherical by using a Marumerizer (a machine, produced by Fuji-Paudra K. K., Japan). The granules were air-dried at a temperature of 60° C. for one hour to obtain dried granules having a diameter of 1.5-3.0 mm. A fluidizing bed was used to apply the coating solution described in Example 2 (10 parts per 100 parts of granules on solid basis). There were obtained granules protected with the coating agent containing each 44% w/w of lysine and methionine.

EXPERIMENT 1

The granules containing methionine, lysine and both of methionine and lysine were respectively prepared by the methods described in Examples 1-5 and Comparative tests 1-4. Each product was used for a dissolution test at pHs of 3.0 and 6.0 respectively corresponding to pHs in the 4th and first stomachs, which was carried out in the following manner: (1) Test conditions:

Test solutions
 pH 3.0, potassium (I) citrate/hydrochloric acid.
 pH 6.8, potassium (I) citrate/NaOH.
Volume—500 ml
Temperature—37° C.
Sample—500 mg
Determination
 Methionine—HPLC method using a column packed with silica gel (Nucleosil C18, commercial product of Nihon Gasukuro K. K., Japan), determined at 210 nm.
 Lysine—Ninhydrin reaction, Optical Density at 565 nm.
Test method—Dissolution test by the paddle method (100 r.p.m.) with reference to The General Method No. 46, Pharmacopoeia of Japan, 11th Edition.

(2) The results are shown in the following Tables 1-3 where EX and CT respectively denote the examples and comparative tests described above.

TABLE 1

| Time | | Dissolution ratio (%) | | | | |
|---|---|---|---|---|---|---|
| | | EX 1 | | EX 2 | | CT 1 | |
| (hour) | pH | 6.0 | 3.0 | 6.0 | 3.0 | 6.0 | 3.0 |
| 0.25 | | 0 | 98.7 | 0 | 72.6 | 0 | 5.1 |
| 0.5 | | 0 | 100 | 0 | 98.5 | 0 | 10.7 |
| 1.0 | | 0 | 100 | 0 | 100 | 0 | 53.0 |
| 2.0 | | 0 | 100 | 0 | 100 | 0 | 79.4 |
| 3.0 | | 0 | 100 | 0 | 100 | 0 | 84.1 |
| 4.0 | | 0 | 100 | 0 | 100 | 0 | 90.1 |
| 5.0 | | 0 | 100 | 0 | 100 | 4.5 | 96.4 |

TABLE 2

| Time | | Dissolution ratio (%) | | | | | |
|---|---|---|---|---|---|---|---|
| | | EX 3 | | CT 2 | | EX 4 | | CT 3 | |
| (hour) | pH | 6.0 | 3.0 | 6.0 | 3.0 | 6.0 | 3.0 | 6.0 | 3.0 |
| 0.5 | | 0 | 80.5 | 0 | 12.7 | 0 | 95.7 | 0 | 22.6 |
| 1.0 | | 0 | 91.9 | 0 | 58.3 | 0 | 100 | 0 | 71.3 |
| 2.0 | | 0 | 98.7 | 0 | 81.6 | 0 | 100 | 0 | 84.5 |
| 3.0 | | 0 | 100 | 7.1 | 90.1 | 0 | 100 | 3.9 | 97.8 |
| 4.0 | | 0 | 100 | 15.3 | 98.8 | 0 | 100 | 10.1 | 100 |
| 5.0 | | 0 | 100 | 26.1 | 100 | 0 | 100 | 20.6 | 100 |

TABLE 3

| Time | pH | Dissolution ratio (%) | | | | | | | |
|---|---|---|---|---|---|---|---|---|---|
| | | EX 5 | | | | CT 4 | | | |
| | | 6.0 | | 3.0 | | 6.0 | | 3.0 | |
| (hour) | | Ly | Me | Ly | Me | Ly | Me | Ly | Me |
| 0.25 | | 0 | 0 | 77.8 | 69.4 | 0 | 0 | 76.4 | 55.3 |
| 0.5 | | 0 | 0 | 100 | 94.3 | 0 | 0 | 100 | 79.9 |
| 1.0 | | 0 | 0 | 100 | 100 | 0 | 0 | 100 | 97.6 |
| 2.0 | | 0 | 0 | 100 | 100 | 5.1 | 0 | 100 | 100 |
| 3.0 | | 0 | 0 | 100 | 100 | 21.1 | 3.9 | 100 | 100 |
| 4.0 | | 0 | 0 | 100 | 100 | 43.2 | 11.8 | 100 | 100 |
| 5.0 | | 0 | 0 | 100 | 100 | 59.9 | 26.3 | 100 | 100 |

Ly = lysine, Me = methionine

Experiment 1 clearly shows that the coating agents according to the present invention are dissolved faster than the comparative coating agent at a pH of 3.0 while better inhibition of solution was noted between them at a pH of 6.0.

EXPERIMENT 2

An animal test was carried out in the following manner to investigate the absorption of the active substance by using 10 sheep (body weight 50-60 kg). Granules were inserted into the headgut messenteric vein, portal fissure vein and carotid artery.

During the test period, each animal was fed with a basic diet consisting of orchard grass and bran (300 g of each), which was fed twice daily at 7 a.m. and 17 p.m.; 600 g. at each meal. Three test feeds were used;
(A) Control feed containing no methionine;
(B) Feed containing untreated granules and (C) Feed containing granules prepared by the method of Example 1 described above. Each feed contained 1.5% (4.5 g) of methionine per 300 g of bran.

7 days after the beginning of the test, blood was collected from the carotid artery of each of the test animals to measure the concentration of methionine in the plasma. The results are shown in Table 4.

TABLE 4

| Sample | Concentration of methionine (n mol/ml) | |
|---|---|---|
| | 11 o'clock | 16 o'clock |
| A | 22.8 ± 1.4 | 28.3 ± 1.2 |
| B | 26.3 ± 0.9 | 30.3 ± 5.0 |
| C | 30.0 ± 1.4 | 38.5 ± 6.7 |

Experiment 2 clearly shows that by addition of a methionine dietary supplement coated with an agent according to the present invention, the concentration of methionine in the plasma increased remarkably in comparison with the results from uncoated granules.

From these findings, it is apparent that the value of dietary supplements and other active substances may greatly be improved by coating them with an agent according to the present invention.

Thus, by virtue of the coating agent according to the present invention, it is possible to effectively protect supplemental active substances for ruminants from degradation in the first stomach and also to improve the availability of the active substances in the 4th stomach.

We claim:

1. A coating agent for delaying the release of a physiologically active substance coated therewith to be administered per os to ruminants, comprising a veterinary-acceptable water-soluble, synthetic high molecular weight compound and an ethylcellulose, in which the ratio of said high molecular weight compound to said ethylcellulose is from 1:0.05 to 1:10 by weight, said coating agent being stable in the first stomach of ruminants and capable of being effectively disintegrated in the 4th stomach of ruminants, wherein said coating agent further includes at least one substance which is miscible in both of said high molecular weight compound and ethylcellulose, is insoluble in water and is solid at room temperature.

2. The coating agent according to claim 1, in which said synthetic high molecular compound is soluble in water at a pH not exceeding 5.

3. The coating agent according to claim 1 or claim 2, in which said synthetic high molecular weight compound is at least one member selected from the group consisting of:
(a) polyvinyl acetal diethylaminoacetate;
(b) copolymers formed with dimethylaminoethyl methacrylate and at least one member selected from the alkyl esters of methacrylic acid acid and the alkyl esters of acrylic acid;
(c) copolymers formed with 2-methyl-5-vinylpyridine and at least one member selected from the group consisting of alkyl esters of acrylic acid and alkyl esters of methacrylic acid, methacrylic acid and acrylic acid and mixtures thereof.

4. The coating agent according to claim 1, in which said water-insoluble substance is selected from the group consisting of one or more saturated fatty acids having more than 14 carbon atoms, hardened oils of animal or plant origin, natural resins and synthetic resins, and mixtures thereof, said substance being soluble in organic solvents.

5. The coating agent according to claim 4, in which said water-insoluble substance is selected from the group consisting of myristic acid, stearic acid, palmitic acid, lauryl alcohol, myristyl alcohol, cetyl alcohol, stearyl alcohol, hardened oil originating from beef tallow, hardened castor oil, shellac and polyvinyl acetate and mixtures thereof.

6. The coating agent according to claim 1 in which the ratio of the high molecular weight compound to said ethylcellulose is from 1:05 to 1:2.0 by weight.

7. The coating agent according to claim 1 in which the ratio of said high molecular weight compound to said water-insoluble substance is more than 50% by weight.

8. A delayed-release veterinary composition for oral administration to ruminants, comprising one or more physiologically active substances coated with a rumen-protecting effective amount of a coating agent as claimed in claim 1.

9. The composition according to claim 8, comprising a core of said physiologically active substances provided with a coating layer formed by spray-drying said coating agent.

10. A composition according to claim 8 in which the ratio of said coating agent to said one or more physiologically active substances is from 5:100 to 100:100 by weight.

11. A process for the preparation of a composition as claimed in claim 8 which process comprises the steps of drying a granule containing at least one active substance and coating said dried granule with at least one coating agent according to claim 1.

12. The process according to claim 11, in which said granule is produced by applying a binder solution to at least one active substance and kneading the mixture to obtain the desired granule.

13. The process according to claim 11, in which said granule is produced by coating at least one active substance with a binder.

14. A process for the preparation of a delayed-release veterinary composition which process comprises the steps of drying a granule containing at least one active substance and coating said dried granule with at least one coating agent according to claim 1.

* * * * *